(12) United States Patent
Kobayashi et al.

(10) Patent No.: US 9,050,326 B2
(45) Date of Patent: Jun. 9, 2015

(54) AMIDO DERIVATIVES-CONTAINED PHARMACEUTICAL COMPOSITION

(75) Inventors: Masanori Kobayashi, Tokyo (JP); Takuya Fukatsu, Tokyo (JP); Kazunari Satou, Tokyo (JP)

(73) Assignee: ASTELLAS PHARMA INC., Tokyo (JP)

(*) Notice: Subject to any disclaimer, the term of this patent is extended or adjusted under 35 U.S.C. 154(b) by 450 days.

(21) Appl. No.: 12/415,295

(22) Filed: Mar. 31, 2009

(65) Prior Publication Data
US 2009/0270463 A1 Oct. 29, 2009

Related U.S. Application Data

(60) Provisional application No. 61/041,704, filed on Apr. 2, 2008.

(51) Int. Cl.
| A61K 31/41 | (2006.01) |
| A01N 43/82 | (2006.01) |
| A61K 31/421 | (2006.01) |
| A61K 9/14 | (2006.01) |
| A61K 9/16 | (2006.01) |
| A61K 31/4192 | (2006.01) |
| A61K 31/4245 | (2006.01) |
| A61K 31/4402 | (2006.01) |

(52) U.S. Cl.
CPC ............. *A61K 31/421* (2013.01); *A61K 9/146* (2013.01); *A61K 9/1652* (2013.01); *A61K 31/4192* (2013.01); *A61K 31/4245* (2013.01); *A61K 31/4402* (2013.01)

(58) Field of Classification Search
None
See application file for complete search history.

(56) References Cited

U.S. PATENT DOCUMENTS

| 6,903,125 B2* | 6/2005 | Kontani et al. ............... 514/364 |
| 2002/0031547 A1 | 3/2002 | Takagi et al. |
| 2003/0003146 A1 | 1/2003 | Takagi et al. |
| 2003/0104063 A1 | 6/2003 | Babcock et al. |
| 2005/0095289 A1 | 5/2005 | Takagi et al. |
| 2005/0130955 A1 | 6/2005 | Ishikura et al. |
| 2007/0014856 A1 | 1/2007 | Takagi et al. |
| 2007/0248681 A1* | 10/2007 | Hoshino et al. ............... 424/494 |
| 2009/0011024 A1 | 1/2009 | Babcock et al. |

FOREIGN PATENT DOCUMENTS

| EP | 1 008 354 A1 | 6/2000 |
| EP | 1 466 914 A1 | 10/2004 |
| EP | 1 652 843 A1 | 5/2006 |
| EP | 1 844 775 A1 | 10/2007 |
| EP | 1 847 260 A2 | 10/2007 |
| JP | 2003 063950 A | 3/2003 |
| JP | 2005/50313 A | 1/2005 |
| JP | 2006-241144 A | 9/2006 |
| JP | 2007-308479 A | 11/2007 |
| WO | WO 96/19239 A1 | 6/1996 |
| WO | WO 98/29137 A1 | 7/1998 |
| WO | 03/000294 A1 | 1/2003 |
| WO | WO 03/055886 A1 | 7/2003 |
| WO | WO 2005/014559 A1 | 2/2005 |
| WO | 2007/079139 A2 | 7/2007 |
| WO | 2007/079139 A3 | 7/2007 |
| WO | 2007/141308 A2 | 12/2007 |

OTHER PUBLICATIONS

Written Opinion of the International Searching Authority; Int. Application No. PCT/JP2009/056607; 2009 (translation).
International Search Report; Int. Application No. PCT/JP2009/056607; Apr. 28, 2009.
Database WPI/Thomson, AN 2003-129615, PN WO02/100379 A1, Takeda Chem. Ind. Ltd., Dec. 19, 2002, Abstract.
Ghebremeskel, A et al., "Use of Surfactants as Plasticizers in Preparing Solid Dispersions of Poorly Soluble API: Stability Testing of Selected Solid Dispersions," Pharmaceutical Research, 23(8):1928-1936, 2006.
Leuner C. et al., "Improving drug solubility for oral delivery using solid dispersions," European J. Pharmaceutics and Biopharmaceutics, 50(1):47-60, 2000.
Pharmaceutical and Food Safety Bureau, Evaluation and Licensing Division, Notification No. 0624001, "Revision of the Guideline on the Impurities in the Medicinal Products with New Active Ingredients," Japanese Ministry of Health, Labor and Welfare, Jun. 2003.
Verreck G et al., "The effect of pressurized carbon dioxide as a temporary plasticizer and foaming agent on the hot stage extrusion process and extrudate properties of solid dispersions of itraconazole with PVP-V 64," European J. Pharmaceutical Sciences, 26(3-4):349-358, 2005.
EP Application No. 09728530.8-1464, Office Action, Jan. 8, 2014, 4 pages.
Hashida, Mitsuru ed., Keikou-touyo-seizai no sekkei to hyoka, Tokyo, Yakugyo Jiho Inc., Feb. 10, 1995, pp. 172-179.
JP Application No. 2010-505925, Notice of Reasons for Rejection (Office Action), mailed Feb. 26, 2013, 5 pages.
European Search Opinion, mailed Oct. 31, 2011, EP application No. 09728530.8, 4 pages.
Canadian Patent Application No. 2,728,890, Office Action, Dec. 18, 2014, 3 pages.
Official Communication, Jan. 23, 2015, European Patent Application No. 09728530.8-764, 3 pages.

* cited by examiner

*Primary Examiner* — Jeffrey S Lundgren
*Assistant Examiner* — Stephanie Springer
(74) *Attorney, Agent, or Firm* — Kilpatrick Townsend & Stockton LLP

(57) ABSTRACT

The present invention relates to a pharmaceutical composition containing a solid dispersion comprising an amide derivative or a salt thereof and a water-soluble polymer, wherein the pharmaceutical composition is not prepared by a melting method. The pharmaceutical composition contains the solid dispersion having an improved oral absorption, properties suitable for formulation, and an excellent stability.

11 Claims, 3 Drawing Sheets

AMIDO DERIVATIVES-CONTAINED PHARMACEUTICAL COMPOSITION

TECHNICAL FIELD

The present invention relates to a solid dispersion containing an amide derivative useful in preventing and treating diseases in which herpesviruses are involved and a water-soluble polymer, and a pharmaceutical composition containing the solid dispersion.

BACKGROUND ART

Patent literature 1 discloses novel amide derivatives useful in preventing and treating diseases in which herpesviruses are involved. In particular, the compound described in Example 27 (hereinafter referred to as compound A) and the compound described in Example 2 (hereinafter referred to as compound B) are considered to be useful. It is expected that the daily dose is generally approximately 0.001 to 50 mg/kg, preferably 0.01 to 30 mg/kg, more preferably 0.05 to 10 mg/kg, for oral administration, and that the daily dose is administered once or divided into multiple doses per day. The dose is appropriately determined depending on each case, in accordance with symptoms, age, sex, and the like.

Because these amide derivatives per se, including compounds A and B, are slightly soluble, it is necessary to improve the solubility and absorption. In addition, it is expected that the dose is approximately 0.001 to 50 mg/kg, and therefore, for large doses, it is necessary to reduce the size of the formulation. Further, a solid dispersion having properties suitable for formulation, for example, a specific volume, compression moldability, or the like, and having an excellent stability is needed.

From the results of toxicity tests, the specification of analogous substances contained in a drug product is, for example, 2% by weight or less, and 0.6% by weight or less in another embodiment, with respect to the amount of the drug substance. Non-patent literature 1 published by the Japanese Ministry of Health, Labor and Welfare in June, 2003 includes a description about the specification of drug products, namely the concept of degradation products (impurities) in drug products as observed at stability tests. According to the description, when the amount of the drug substance to be administered per day is 10 mg or more to less than 2 g, the threshold of a degradation product requiring safety qualification in a drug product is a lower one of either 0.2% as the percentage of the degradation product contained in a drug substance or 2 mg as the total daily intake of the degradation product. Therefore, when the drug product contains, for example, 200 mg of the drug substance, the specification of a degradation product which can be generally determined without any safety qualification of the degradation product is preferably 0.2% or less as the percentage of the degradation product contained in a drug substance. The drug product will be put on the market based on the results of clinical trials.

Formulations containing compound A (N-(2,6-Dimethylphenyl)-N-(2-{[4-(1,2,4-oxadiazol-3-yl)phenyl]amino}-2-oxoethyl)tetrahydro-2H-thiopyran-4-carboxamide 1,1-dioxide) are 50 mg tables, 100 mg tablets, and 200 mg tablets. To ensure the stability of these formulations, the ratio of the main degradation product (hereinafter referred to as F1) of compound A (N-(2,6-Dimethylphenyl)-N-(2-{[4-(1,2,4-oxadiazol-3-yl)phenyl]amino}-2-oxoethyl)tetrahydro-2H-thiopyran-4-carboxamide 1,1-dioxide) with respect to the sum of compound A (N-(2,6-Dimethylphenyl)-N-(2-{[4-(1,2,4-oxadiazol-3-yl)phenyl]amino}-2-oxoethyl)tetrahydro-2H-thiopyran-4-carboxamide 1,1-dioxide) and degradation products thereof should be, for example, 2% by weight or less, 0.6% by weight or less in another embodiment, 0.2% by weight or less in still another embodiment.

As a method for solubilizing a slightly soluble drug, patent literature 2 discloses a solid composition containing an extremely hardly water soluble drug in the form of an amorphous substance, a polymer base, and a nonionic surfactant, to solve problems as observed in conventional solid dispersion, that is, to improve the decreased dissolution rate of a solid dispersion, or a decreased solubility caused by drug precipitation after a certain period of time.

However, patent literature 2 does not refer to the compound of the formula (I), and further improvements are necessary to prepare a pharmaceutical composition.

CITATION LIST

Patent Literature

[patent literature 1] WO 2005/014559
[patent literature 2] WO 96/19239
[non-patent literature 1] Pharmaceutical and Food Safety Bureau, Evaluation and Licensing Division Notification No. 0624001 "Revision of the Guideline on the Impurities in the Medicinal Products with New Active Ingredients"

SUMMARY OF INVENTION

Technical Problem

The present invention provides a solid dispersion having the properties described above, and a pharmaceutical composition containing the solid dispersion.

Salts, a clathrate, a solid dispersion, and the like are known as methods of improving the solubility of a slightly water-soluble drug. However, with respect to compound A per se, it is expected that a salt of compound A is desalted, even if the solubility is improved, and that the inclusion ability of cyclodextrin, which is commonly used as a host of clathrates, is low. In addition, it was found that compound A had a low chemical stability against heat in a process of manufacturing a solid dispersion using a twin screw extruder as one of the melting methods.

Solution to Problem

The present inventors paid attention to and examined the properties of compound A against heat, and found that the melting point of compound A was close to the decomposition point thereof. While focusing on the properties of compound A, the present inventors have conducted inventive studies on improving the solubility of compound A and provision of a stable pharmaceutical composition, and as a result, completed the present invention.

The present invention relates to 1. a pharmaceutical composition comprising a solid dispersion containing a compound of the general formula (I) and a water-soluble polymer, wherein the pharmaceutical composition is not prepared by a melting method, and the compound is an amide derivative of the general formula (I) or a salt thereof,

[Chem. 1]

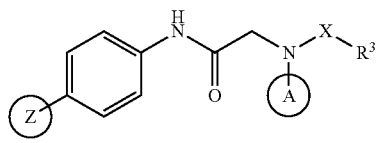

[the symbols used in the formula (I) mean as follows:
Z: Z is a 1,2,4-oxadiazol-3-yl, 4-oxazolyl, 1,2,3-triazol-2-yl, or 2-pyridyl group;
A: A is an aryl which may have a substituent, heteroaryl which may have a substituent, saturated hydrocarbon ring-fused aryl which may have a substituent, or saturated heterocyclic ring-fused aryl group which may have a substituent, with the proviso that the saturated hydrocarbon ring-fused aryl or saturated heterocyclic ring-fused aryl group is bound to a nitrogen atom via a carbon atom in an aromatic ring;
X: X is CO or $SO_2$;
$R^3$: $R^3$ is an alkyl which may have a substituent, alkenyl which may have a substituent, alkynyl which may have a substituent, cycloalkyl which may have a substituent, cycloalkenyl which may have a substituent, aryl which may have a substituent, or heterocyclic group which may have a substituent, or NRaRb; and
Ra and Rb: Ra and Rb are the same or different from each other, and are H, a lower alkyl, lower alkenyl, lower alkynyl, cycloalkyl, cycloalkenyl, aryl, 5- or 6-membered monocyclic heteroaryl which has 1 to 4 heteroatoms selected from the group consisting of N, S and O, or lower alkylene-aryl group],
2. the pharmaceutical composition of 1 wherein
Z is a 1,2,4-oxadiazol-3-yl or 4-oxazolyl group;
A is a phenyl which is substituted with at least one methyl group and may further have 1 to 2 substituents selected from the group consisting of a methyl group and a halogen atom, or 5-indanyl group;
X is CO; and
$R^3$ is a 1,1-dioxide tetrahydro-2H-thiopyran-4-yl group,
3. the pharmaceutical composition of 1, wherein the compound of the formula (I) is a compound selected from the group consisting of:
N-(4-methylphenyl)-N-(2-{[4-(1,3-oxazol-4-yl)phenyl]amino}-2-oxoethyl)tetrahydro-2H-thiopyran-4-carboxamide 1,1-dioxide);
N-(4-methylphenyl)-N-(2-{[4-(1,2,4-oxadiazol-3-yl)phenyl]amino}-2-oxoethyl)tetrahydro-2H-thiopyran-4-carboxamide 1,1-dioxide;
N-(2,6-dimethylphenyl)-N-(2-{[4-(1,2,4-oxadiazol-3-yl)phenyl]amino}-2-oxoethyl)tetrahydro-2H-thiopyran-4-carboxamide 1,1-dioxide;
N-(3-fluoro-4-methylphenyl)-N-(2-{[4-(1,2,4-oxadiazol-3-yl)phenyl]amino}-2-oxoethyl)tetrahydro-2H-thiopyran-4-carboxamide 1,1-dioxide; and
N-(4-chloro-3-methylphenyl)-N-(2-{[4-(1,2,4-oxadiazol-3-yl)phenyl]amino}-2-oxoethyl)tetrahydro-2H-thiopyran-4-carboxamide 1,1-dioxide,
4. the pharmaceutical composition of 1, wherein the compound of the formula (I) is N-(2,6-Dimethylphenyl)-N-(2-{[4-(1,2,4-oxadiazol-3-yl)phenyl]amino}-2-oxoethyl)tetrahydro-2H-thiopyran-4-carboxamide 1,1-dioxide,
5. the pharmaceutical composition of 1, wherein the water-soluble polymer is a polymer or two or more polymers selected from the group consisting of hydroxypropylmethyl cellulose, copolyvidone, povidone, and hydroxypropyl cellulose,
6. the pharmaceutical composition of 1, wherein the amount of the water-soluble polymer is 0.1 to 10 parts by weight, with respect to 1 part by weight of the compound of the formula (I),
7. the pharmaceutical composition of 1, wherein the specific volume of the solid dispersion is 2 to 25 mL/g,
8. the pharmaceutical composition of 1, wherein a tablet hardness is 5 to 300 N when 100 mg of the solid dispersion is formed into tablets using a flat punch of 7.5 mm in diameter under a tabletting pressure of 2 kN,
9. the pharmaceutical composition of 1, further comprising a disintegrator,
10. the pharmaceutical composition of any one of 1 to 9, prepared by a process comprising the steps of:
dissolving and/or suspending the compound of the formula (I) and the water-soluble polymer in a pharmaceutically acceptable solvent, and
removing the solvent by spray drying to prepare the solid dispersion,
11. the pharmaceutical composition of 10, wherein the pharmaceutically acceptable solvent is one solvent, or two or more solvents selected from the group consisting of ketones, alcohols, and water,
12. the pharmaceutical composition prepared by the process described in 11, wherein the pharmaceutically acceptable solvent is a mixture of ketones, alcohols, or a mixed solvent thereof, with water, and the content of water in the pharmaceutically acceptable solvent is more than 0% by weight to less than 50% by weight,
13. a process of manufacturing a solid dispersion, comprising the steps of: dissolving and/or suspending a compound of the formula (I) and a water-soluble polymer in a pharmaceutically acceptable solvent, and
removing the solvent by spray drying to prepare the solid dispersion.

Advantageous Effects of Invention

The present invention is characterized in that (1) since compound A is slightly water-soluble, the solubility and oral absorption can be improved by mixing compound A with a water-soluble polymer as a carrier to form a solid dispersion (hereinafter referred to as SDF), (2) since, due to the large dose of compound A, SDF properties considerably affect the properties of the formulation, an SDF having a decreased amount of the carrier and having properties such as an appropriate hardness which can impart a good compression moldability to the formulation can be provided, (3) although compound A is easily decomposed by heat, compound A can be stabilized, and the like.

DESCRIPTION OF EMBODIMENTS

Figure 1:
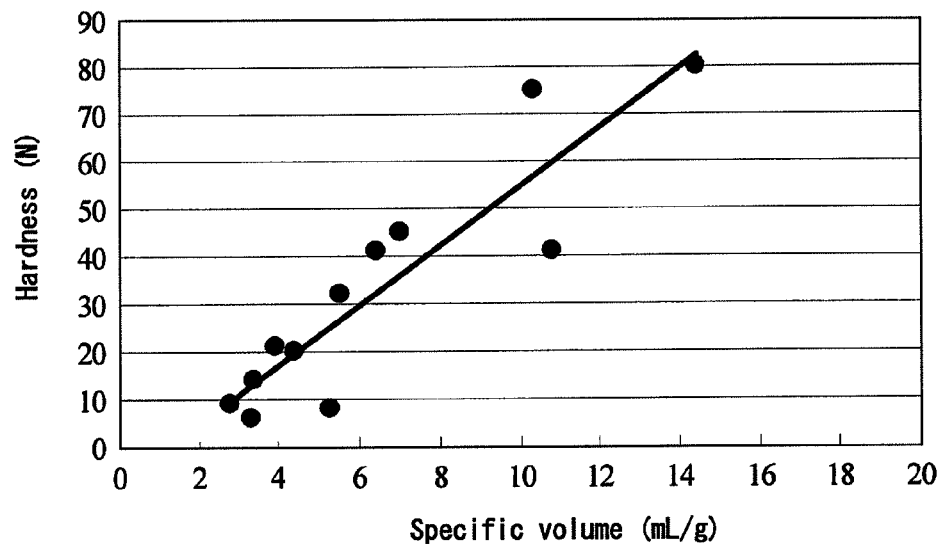
FIG. 1 is a graph showing the relationship between the specific volumes and the hardnesses of the solid dispersions prepared in Examples 1, 5, 8, 13, 14, 17, 19, 23, 28, 44, 49, 50, 51, and 52.
Figure 2:
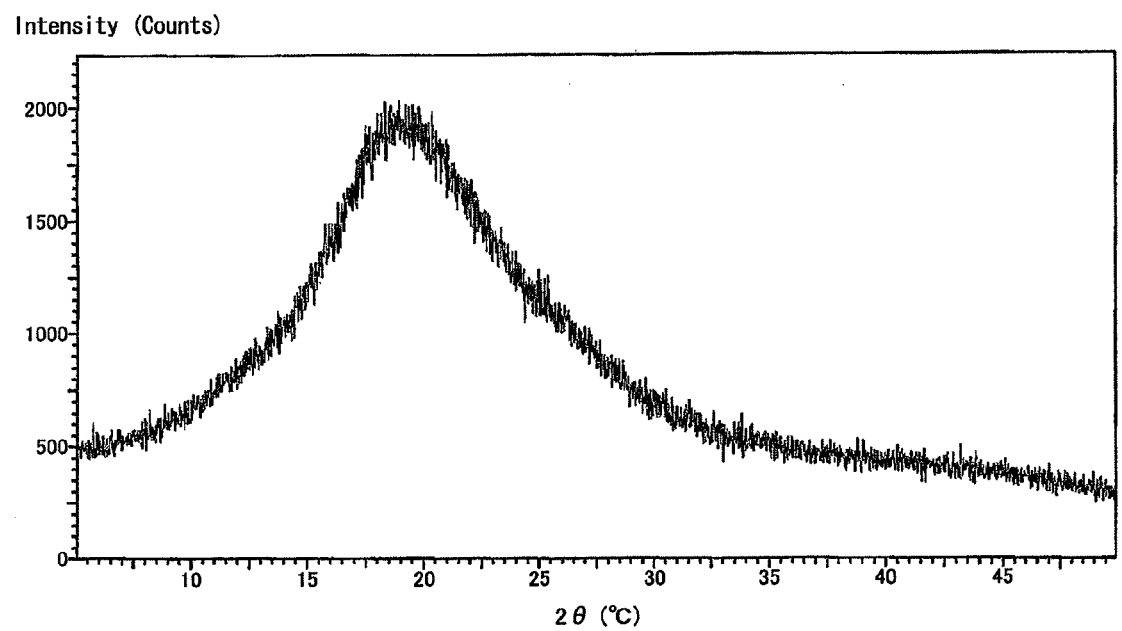
FIG. 2 is an X-ray diffraction spectrum of the solid dispersion prepared in Example 1, obtained by measuring it immediately after its preparation.
Figure 3:
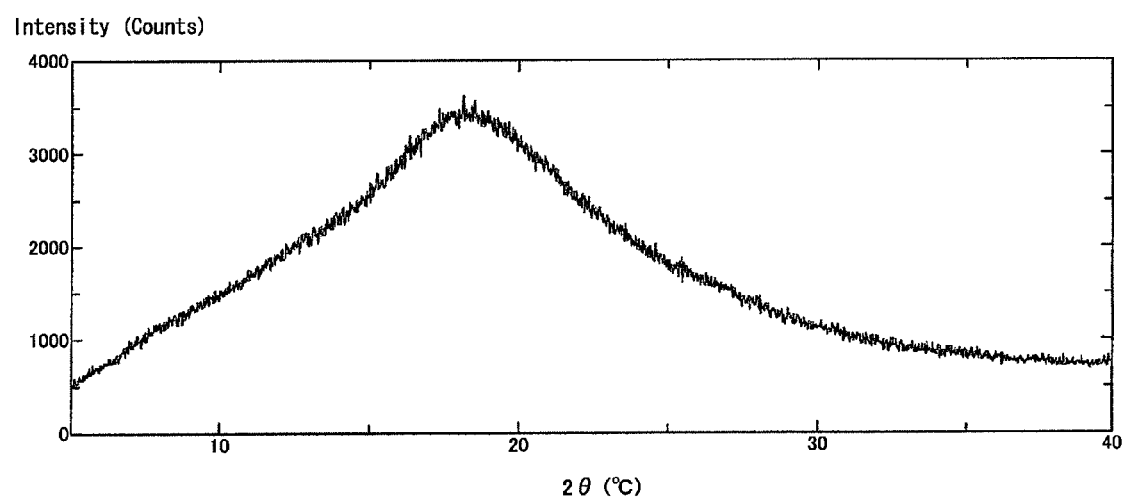
FIG. 3 is an X-ray diffraction spectrum of the solid dispersion prepared in Example 44, obtained by measuring it immediately after its preparation.
Figure 4:
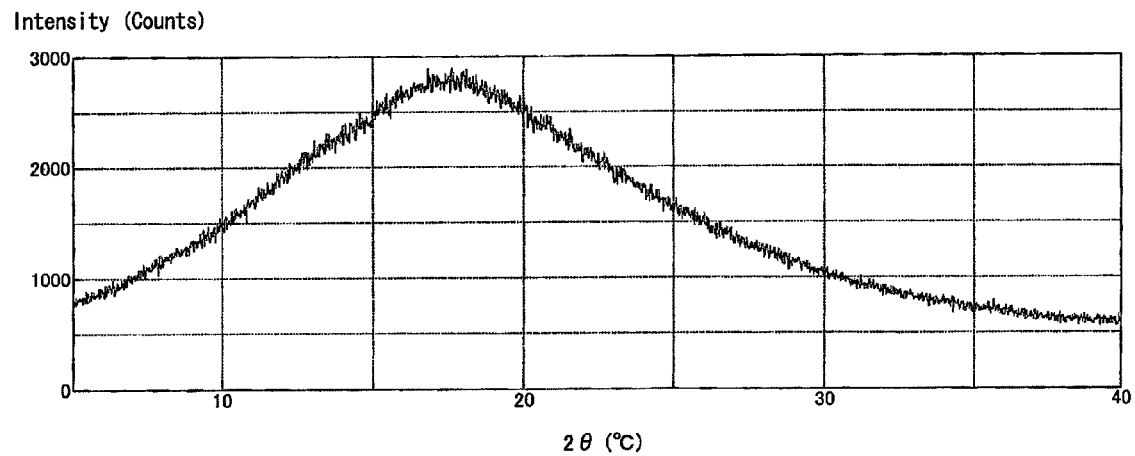
FIG. 4 is an X-ray diffraction spectrum of the solid dispersion prepared in Example 53, obtained by measuring it immediately after its preparation.
Figure 5:
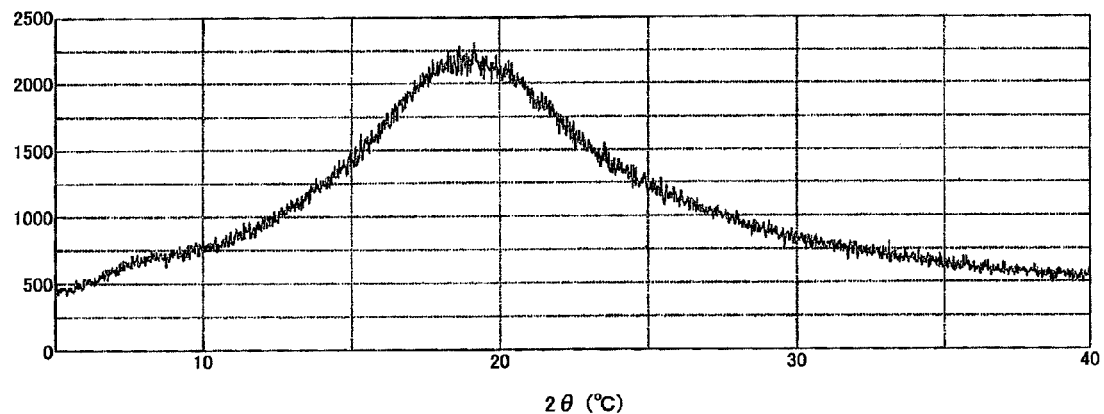
FIG. 5 is an X-ray diffraction spectrum of the solid dispersion prepared in Example 54, obtained by measuring it immediately after its preparation.

The embodiments of the present invention will be explained in detail hereinafter.

The term "to improve solubility" as used herein means that a solubility of compound A in water, a buffer, or the like is increased. More particularly, for example, when a solid dispersion, or a pharmaceutical composition containing a solid dispersion is evaluated by a dissolution test, it is defined as, for example, that the solubility of compound A in the form of a solid dispersion (or compound A contained in a solid dispersion of compound A) is 2 or more times higher than that of compound A per se, 5 or more times higher than that of compound A per se in another embodiment, and 10 or more times higher than that of compound A per se in still another embodiment.

The term "stable" as used herein means to have stability against, for example, heat, temperature, or humidity. It is defined as, for example, that substances analogous to compound A contained in a pharmaceutical composition account for 2% or less by weight, 0.6% or less by weight in another embodiment, and 0.2% or less by weight in still another embodiment, with respect to the total amount of compound A.

The term "hardness of solid dispersion" as used herein means the hardness of a tablet obtained by forming 100 mg of the solid dispersion of compound A into tablets using a flat punch of 7.5 mm in diameter under a tabletting pressure of 2 kN.

The compound of the general formula (I) used in the present invention is useful as a novel amide derivative useful in preventing and treating diseases in which herpesviruses are involved (as disclosed in WO 2005/014559).

An amide derivative of the general formula (I) or a salt thereof,

[Chem. 2]

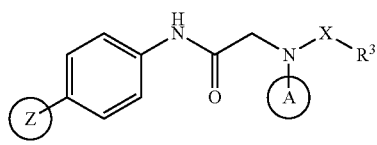
(I)

[the symbols used in the formula (I) mean as follows:
Z: Z is a 1,2,4-oxadiazol-3-yl, 4-oxazolyl, 1,2,3-triazol-2-yl, or 2-pyridyl group;
A: A is an aryl which may have a substituent, heteroaryl which may have a substituent, saturated hydrocarbon ring-fused aryl which may have a substituent, or saturated heterocyclic ring-fused aryl group which may have a substituent, with the proviso that the saturated hydrocarbon ring-fused aryl or saturated heterocyclic ring-fused aryl group is bound to a nitrogen atom via a carbon atom in an aromatic ring;
X: X is CO or SO$_2$;
R$^3$: R$^3$ is an alkyl which may have a substituent, alkenyl which may have a substituent, alkynyl which may have a substituent, cycloalkyl which may have a substituent, cycloalkenyl which may have a substituent, aryl which may have a substituent, or heterocyclic group which may have a substituent, or NRaRb; and
Ra and Rb: Ra and Rb are the same or different from each other, and are H, a lower alkyl, lower alkenyl, lower alkynyl, cycloalkyl, cycloalkenyl, aryl, 5- or 6-membered monocyclic heteroaryl which has 1 to 4 heteroatoms selected from the group consisting of N, S and O, or lower alkylene-aryl group].

Another embodiment is a pharmaceutical composition, wherein Z is a 1,2,4-oxadiazol-3-yl or 4-oxazolyl group; A is a phenyl which is substituted with at least one methyl group and may further have 1 to 2 substituents selected from the group consisting of a methyl group and a halogen atom, or 5-indanyl group; X is CO; and R$^3$ is a 1,1-dioxide tetrahydro-2H-thiopyran-4-yl group.

As still another embodiment, the compound of the formula (I) is a compound selected from the group consisting of:
N-(4-methylphenyl)-N-(2-{[4-(1,3-oxazol-4-yl)phenyl]amino}-2-oxoethyl)tetrahydro-2H-thiopyran-4-carboxamide 1,1-dioxide);
N-(4-methylphenyl)-N-(2-{[4-(1,2,4-oxadiazol-3-yl)phenyl]amino}-2-oxoethyl)tetrahydro-2H-thiopyran-4-carboxamide 1,1-dioxide;
N-(2,6-dimethylphenyl)-N-(2-{[4-(1,2,4-oxadiazol-3-yl)phenyl]amino}-2-oxoethyl)tetrahydro-2H-thiopyran-4-carboxamide 1,1-dioxide;
N-(3-fluoro-4-methylphenyl)-N-(2-{[4-(1,2,4-oxadiazol-3-yl)phenyl]amino}-2-oxoethyl)tetrahydro-2H-thiopyran-4-carboxamide 1,1-dioxide; and
N-(4-chloro-3-methylphenyl)-N-(2-{[4-(1,2,4-oxadiazol-3-yl)phenyl]amino}-2-oxoethyl)tetrahydro-2H-thiopyran-4-carboxamide 1,1-dioxide.

As still another embodiment, the compound of the formula (I) is the compound described in Example 27 (hereinafter referred to as compound A) and the compound described in Example 2 (hereinafter referred to as compound B) of WO 2005/014559.

As still another embodiment, the compound of the formula (I) is compound A (chemical name: N-(2,6-dimethylphenyl)-N-(2-{[4-(1,2,4-oxadiazol-3-yl)phenyl]amino}-2-oxoethyl) tetrahydro-2H-thiopyran-4-carboxamide 1,1-dioxide).

With respect to the amount of the compound of the formula (I), the daily dose of the compound of the formula (I) is generally approximately 0.001 to 50 mg/kg, 0.01 to 30 mg/kg in another embodiment, and 0.05 to 10 mg/kg in still another embodiment, for oral administration. The daily dose is administered once or divided into multiple doses per day. It is expected that the dose is appropriately determined depending on each case, in accordance with symptoms, age, sex, and the like.

The content of the drug contained in the solid dispersion is not particularly limited, so long as the solid dispersion may be formed, but is, for example, 1 to 99% by weight, and 1 to 50% by weight in another embodiment, in the solid dispersion. The amount of the drug contained in the formulation is, for example, 1 to 99% by weight, and 1 to 50% by weight in another embodiment.

The water-soluble polymer used in the present invention is not particularly limited, so long as the compound of the formula (I) can be carried as the solid dispersion. Examples of the water-soluble polymer include hydroxypropylmethylcellulose (hereinafter referred to as HPMC), copolyvidone, povidone, hydroxypropylcellulose (hereinafter referred to as HPC), and the like. TC5E, TC5R, or the like may be used as HPMC. Kollidon VA 64 or the like, Kollidon or the like, and HPC-L, HPC-SL, or the like, may be used as copolyvidone, povidone, and HPC, respectively. These water-soluble polymers may be used alone or as an appropriate combination of two or more thereof.

More particularly, product name TC-5E (viscosity: 3 mPa·s, 2% W/V aqueous solution, 20° C., Shin-Etsu Chemical Co., Ltd.), product name TC-5R (viscosity: 6 mPa·s, 2% W/V aqueous solution, 20° C., Shin-Etsu Chemical Co., Ltd.), product name TC-5S (viscosity: 15 mPa·s, 2% W/V aqueous solution, 20° C., Shin-Etsu Chemical Co., Ltd.), product name Methocel E3 (viscosity: 3 mPa·s, 2% W/V aqueous solution, 20° C., Dow Chemical), product name Methocel E5 (viscosity: 5 mPa·s, 2% W/V aqueous solution, 20° C., Dow Chemical), product name Methocel E15 (viscosity: 15 mPa·s, 2% W/V aqueous solution, 20° C., Dow Chemical), or the like may be used as HPMC. A low viscosity grade of HPC (viscosity: 2 to 10 mPa·s, 2% W/V aqueous solution, 20° C.), such as product name HPC-SSL (viscosity: 3.0 to 5.9 mPa·s, 2% W/V aqueous solution, 20° C., Nippon Soda Co., Ltd.), product name HPC-SL (viscosity: 2.0 to 2.9 mPa·s, 2% W/V aqueous solution, 20° C., Nippon Soda Co., Ltd.), or product name HPC-L (viscosity: 6.0 to 10.0 mPa·s, 2% W/V aqueous solution, 20° C., Nippon Soda Co., Ltd.), is preferable as HPC. Product names Kollidon VA 64 (BASF Japan Ltd.), Kollidon VA 64 Fine (BASF Japan Ltd.), Plasdone S-630 (ISP Japan Ltd.), or the like may be used as copolyvidone. Product names povidone (Gokyo Trading Co. Ltd.), Kollidon (BASF Japan Ltd.), Plasdone (ISP Japan Ltd.), Aiphtact K-30 (Dai-ichi Kogyo Seiyaku Co., Ltd.), or the like may be used as povidone.

The content of the water-soluble polymer is not particularly limited, so long as the compound of the formula (I) can be carried as the solid dispersion, but is generally 0.1 to 10 parts by weight, 0.1 to 5 parts by weight in another embodiment, and 0.25 to 3 parts by weight in still another embodiment, with respect to 1 part by weight of the compound of the formula (I).

The solid dispersion comprising the compound of the formula (I) in the present invention and the water-soluble polymer is further mixed with one or more pharmaceutically acceptable additives to prepare a pharmaceutical composition.

The additives are not particularly limited, so long as they are pharmaceutically acceptable. Examples of the additives include a filler, a binder, a disintegrator, an acidulant, an effervescent agent, an artificial sweetener, a flavor, a lubricant, a coloring agent, a stabilizing agent, a buffer, an antioxidant, and the like.

The filler may be selected from, for example, mannitol, lactose, corn starch, or the like.

The binder may be selected from, for example, hydroxypropylmethyl cellulose, hydroxypropyl cellulose, polyvinyl alcohol, methyl cellulose, gum arabic, or the like.

The disintegrator may be selected from, for example, corn starch, starches, crystalline cellulose, carmellose calcium, carmellose sodium, light anhydrous silicic acid, calcium silicate, low-substituted hydroxypropyl cellulose, partially pregelatinized starch, sodium carboxymethyl starch, agar powder, crospovidone, synthetic aluminum silicate, sucrose fatty acid esters, lactose hydrate, D-mannitol, anhydrous citric acid, or the like.

The acidulant may be selected from, for example, citric acid, tartaric acid, malic acid, or the like.

The effervescent agent may be selected from, for example, sodium bicarbonate or the like.

The artificial sweetener may be selected from, for example, saccharin sodium, dipotassium glycyrrhizinate, aspartame, stevia, thaumatin, or the like.

The flavor may be selected from, for example, lemon, lemon-lime, orange, menthol, or the like.

The lubricant may be selected from, for example, magnesium stearate, calcium stearate, sucrose fatty acid esters, polyethylene glycol, talc, stearic acid, or the like.

The coloring agent may be selected from, for example, yellow ferric oxide, red ferric oxide, food yellow No. 4, food yellow No. 5, food red No. 3, food red No. 102, food blue No. 3, or the like.

The buffer may be selected from, for example, citric acid, succinic acid, fumaric acid, tartaric acid, ascorbic acid, or salts thereof; glutamic acid, glutamine, glycine, aspartic acid, alanine, arginine, or salts thereof; magnesium oxide, zinc oxide, magnesium hydroxide, phosphoric acid, boric acid, or their salts; or the like.

The antioxidant may be selected from, for example, ascorbic acid, dibutyl hydroxytoluene, propyl gallate, or the like.

These additives may be added alone in an appropriate amount, or as a combination of two or more thereof in appropriate amounts.

A process of manufacturing the solid dispersion comprising the compound of the general formula (I) and the water-soluble polymer, and a process of manufacturing the pharmaceutical composition comprising the solid dispersion, according to the present invention, will be explained in detail hereinafter.

The solid dispersion in the present invention is prepared by dissolving and/or suspending the compound of the general formula (I) and the water-soluble polymer in a pharmaceutically acceptable solvent, and removing the solvent.

The pharmaceutically acceptable solvent used in the present invention is not particularly limited, so long as the compound of the general formula (I) can be maintained in an amorphous state in the presence of the water-soluble polymer. Examples of the pharmaceutically acceptable solvent include ketones such as acetone, alcohols such as methanol, ethanol, or propanol, a mixture thereof, and a mixed solvent of water with one or more of these solvent. These pharmaceutically acceptable solvents may be used alone or as an appropriate combination of two or more thereof. The mixed solvent of water with acetone is preferred. The content of water is preferably higher than 0% by weight to lower than 50% by weight, with respect to the amount of the pharmaceutically acceptable solvent. The ratio of acetone to water (acetone:water) is, for example, 9.9:0.1 to 0.1:9.9, 9.5:0.5 to 5.0:5.0 in another embodiment, and 9.5:0.5 to 8.5:1.5 in still another embodiment. Alternatively, the ratio of acetone to water (acetone:water) is, for example, 10.0:0.0 to 0.1:9.9, 10.0:0.0 to 5.0:5.0 in another embodiment, 10.0:0.0 to 6.0:4.0 in still another embodiment, and 9.5:0.5 to 8.5:1.5 in still another embodiment.

The amount of the pharmaceutically acceptable solvent is not particularly limited, so long as it is enough to render the compound of the general formula (I) amorphous. A 1- to 100-fold amount (w/w) of the pharmaceutically acceptable solvent, or a 5- to 20-fold amount (w/w) of the pharmaceutically acceptable solvent in another embodiment may be contained, with respect to the total weight of the compound of the general formula (I) and the water-soluble polymer.

A method of removing the pharmaceutically acceptable solvent used in the present invention is not particularly limited, so long as the solvent can be removed from the liquid in which the compound of the general formula (I) and the water-soluble polymer are dissolved and/or suspended. Examples of the method include spray drying, drying under reduced pressure, forced-air drying, and the like, and spray drying may be used in another embodiment.

In the process of manufacturing the solid dispersion according to the present invention, the solid dispersion is prepared by dissolving and/or suspending the compound of the general formula (I) and the water-soluble polymer in the pharmaceutically acceptable solvent, and removing the solvent.

The process of the present invention can comprise known methods per se, for example, a step of pulverizing the compound (I), the water-soluble polymer, and additives, a step of mixing these components, a step of dissolving and/or suspending the resulting mixture to the pharmaceutically acceptable solvent, a step of spray drying, a step of drying under reduced pressure, a mixing step, a sifting step, or the like.

The specific volume of the solid dispersion in the present invention correlates with the compression moldability of the solid dispersion. Since an additive capable of improving compression moldability as well as the solid dispersion is generally added to tablets to increase the hardness of the tablets, the tablet size tends to become large. In the present invention, an increased specific volume of the solid dispersion improves the compression moldability, allows a reduction in the size of tablets, and imparts an excellent tablet hardness for production and distribution of medicaments.

It is considered that the specific volume is affected by the content of water, and the temperature at the nozzle exit of the spray dryer for removing the pharmaceutically acceptable solvent after the compound of the general formula (I) and the water-soluble polymer are dissolved and/or suspended in the pharmaceutically acceptable solvent. The exit temperature is generally 50 to 100° C., 60 to 75° C. in another embodiment, and 68 to 72° C. in still another embodiment. The content of water is preferably higher than 0% by weight to lower than 50% by weight, with respect to the amount of the pharmaceutically acceptable solvent. For example, when the pharmaceutically acceptable solvent is a mixed solvent of acetone and water, the ratio (acetone:water) is generally 9.9:0.1 to 0.1:9.9, 9.5:0.5 to 5.0:5.0 in another embodiment, and 9.5:0.5 to 8.5:1.5 in still another embodiment. Alternatively, the ratio of acetone to water (acetone:water) is, for example, 10.0:0.0 to 0.1:9.9, 10.0:0.0 to 5.0:5.0 in another embodiment, and 10.0:0.0 to 8.5:1.5 in still another embodiment. The spray pressure is 0.1 to 0.8 MPa, and 0.3 to 0.4 MPa in another embodiment. The rotary disk rotation speed is 1000 to 20000 rpm, and 10000 to 20000 rpm in another embodiment. The spray rate is 1 to 1000 g/min, 5 to 100 g/min in another embodiment, and 50 to 100 g/min in still another embodiment.

The specific volume of the solid dispersion is not particularly limited, so long as it does not affect the compression moldability of the pharmaceutical composition containing the solid dispersion of the compound of the general formula (I), but is generally 2 to 15 mL/g, and 5 to 10 mL/g in another embodiment. Alternatively, the specific volume is 2 to 25 mL/g, 2 to 20 mL/g in another embodiment, and 5 to 15 mL/g in still another embodiment. When the specific volume is less than 2 mL/g, the compression moldability tends to become low. When the specific volume is more than 15 mL/g, it is considered unsuitable for industrial production. The hardness of the solid dispersion of the compound of the general formula (I) is not particularly limited, so long as it does not affect the compression moldability of the pharmaceutical composition containing the solid dispersion, but is, for example, 5 to 300 N, 5 to 100 N in another embodiment, and 10 to 80 N in still another embodiment, for example, when 100 mg of the solid dispersion is formed into tablets using a flat punch of 7.5 mm in diameter under a tabletting pressure of 2 kN.

In the process of manufacturing the pharmaceutical composition (formulation) of the present invention, the solid dispersion may be mixed with a pharmaceutically acceptable additive to prepare the pharmaceutical composition. For example, the solid dispersion is mixed with one additive, or two or more additives, and known methods per se are carried out to obtain tablets, or capsules prepared by filling, for example, hard gelatin capsules with fine-granules or granules. The process of manufacturing the pharmaceutical composition or its pharmaceutical formulation according to the present invention is not particularly limited, so long as it can produce the desired pharmaceutical formulation by using an appropriate combination of the above methods or known methods per se.

A tablet hardness may be appropriately selected in accordance with the size and the shape of the tablet, but is generally, for example, 20 to 200 N, and 50 to 150 N in another embodiment, in a case of, for example, a 500 mg tablet (containing 200 mg as compound A), taking into consideration handling in production, distribution, and the like of medicaments. Alternatively, the tablet hardness is, for example, 20 to 300 N, 50 to 250 N in another embodiment, and 50 to 200 N in still another embodiment. When the hardness is less than 20 N, it is concerned that tablets may be disintegrated in production or distribution of medicaments.

After being formed into tablets, the surfaces of the tablets may be optionally coated with film.

The coating is not particularly limited, so long as it is a pharmaceutically-used coating method. Film-coating agents may be added alone in an appropriate amount, or as a combination of two or more thereof in appropriate amounts. A coating rate is not particularly limited, so long as film can be formed.

EXAMPLES

The present invention will now be further illustrated by, but is by no means limited to, the following Examples, Comparative Examples, and Experimental Examples. Compound A as used herein was prepared in accordance with the method described in WO 2005/014559.

"Specific Volume":

Using a powder property determination device (Powder Tester PT-D, manufactured by Hosokawa Micron Corporation), a predetermined amount of a sample is placed on a 20 mesh sieve, and continuously allowed to fall naturally through a funnel into a receptacle with an inner capacity of 100 mL while being vibrated. After the pile of the sample is scraped off of the receptacle with a flat metal plate, the mass of the receptacle into which the sample has been introduced is weighed and a specific volume is calculated.

"Hardness":

A hardness is measured by using a Tablet Hardness Tester "Schleuniger" Model 6D (manufactured by Schleuniger).

Example 1

After 4000 g of compound A and 2000 g of HPMC were dissolved in 54 kg of acetone and 6 kg of water (9:1), a spray dryer was used at an exhaust temperature of 70° C., a spray pressure of 0.3 MPa, and a spray rate of 100 g/min to obtain a solid dispersion of the present invention.

Example 2

After 4000 g of compound A and 2000 g of HPMC were dissolved in 51 kg of acetone and 9 kg of water (8.5:1.5), a spray dryer was used at an exhaust temperature of 70° C., a spray pressure of 0.4 MPa (BN160S-IS), and a spray rate of 100 g/min to obtain a solid dispersion of the present invention.

Example 3

After 4000 g of compound A and 2000 g of HPMC were dissolved in 48 kg of acetone and 12 kg of water (8:2), a spray dryer was used at an exhaust temperature of 60° C., a spray pressure of 0.4 MPa (BN160S-IS), and a spray rate of 100 g/min to obtain a solid dispersion of the present invention.

Example 4

After 4000 g of compound A and 2000 g of HPMC were dissolved in 54 kg of acetone and 6 kg of water (9:1), a spray dryer was used at an exhaust temperature of 70° C., an rotary disk rotation speed of 15000 rpm, and a spray rate of 100 g/min to obtain a solid dispersion of the present invention.

Example 5

After 4000 g of compound A and 2000 g of HPMC were dissolved in 54 kg of acetone and 6 kg of water (9:1), a spray dryer was used at an exhaust temperature of 80° C., a spray pressure of 0.4 MPa (BN160S-IS), and a spray rate of 100 g/min to obtain a solid dispersion of the present invention.

Example 6

After 800 g of compound A and 400 g of HPMC were dissolved in 10.2 kg of acetone and 1.8 kg of water (8.5:1.5), a spray dryer was used at an exhaust temperature of 62° C., a spray pressure of 0.4 MPa (BN160S-IS), and a spray rate of 100 g/min to obtain a solid dispersion of the present invention.

Example 7

After 800 g of compound A and 400 g of HPMC were dissolved in 10.2 kg of acetone and 1.8 kg of water (8.5:1.5), a spray dryer was used at an exhaust temperature of 59° C., a spray pressure of 0.4 MPa (BN160S-IS), and a spray rate of 100 g/min to obtain a solid dispersion of the present invention.

Example 8

After 400 g of compound A and 200 g of HPMC were dissolved in 5.4 kg of acetone and 0.6 kg of water (9:1), a spray dryer was used at an exhaust temperature of 60° C., a spray pressure of 0.4 MPa (BN160S-IS), and a spray rate of 100 g/min to obtain a solid dispersion of the present invention.

Example 9

After 666 g of compound A and 333 g of HPMC were dissolved in 8.0 kg of acetone and 2.0 kg of water (8:2), a spray dryer was used at an exhaust temperature of 60° C., a spray pressure of 0.4 MPa (BN160S-IS), and a spray rate of 50 g/min to obtain a solid dispersion of the present invention.

Example 10

After 666 g of compound A and 333 g of HPMC were dissolved in 8.0 kg of acetone and 2.0 kg of water (8:2), a spray dryer was used at an exhaust temperature of 60° C., a spray pressure of 0.4 MPa (BN160S-IS), and a spray rate of 75 g/min to obtain a solid dispersion of the present invention.

Example 11

After 667 g of compound A and 333 g of HPMC were dissolved in 8.0 kg of acetone and 2.0 kg of water (8:2), a spray dryer was used at an exhaust temperature of 60° C., a spray pressure of 0.4 MPa (BN160S-IS), and a spray rate of 100 g/min to obtain a solid dispersion of the present invention.

Example 12

After 667 g of compound A and 333 g of HPMC were dissolved in 8.0 kg of acetone and 2.0 kg of water (8:2), a spray dryer was used at an exhaust temperature of 65° C., a spray pressure of 0.4 MPa (BN160S-IS), and a spray rate of 100 g/min to obtain a solid dispersion of the present invention.

Example 13

After 1000 g of compound A and 500 g of HPMC were dissolved in 13.5 kg of acetone and 1.5 kg of water (9:1), a spray dryer was used at an exhaust temperature of 70° C., a spray pressure of 0.3 MPa (BN160S-IS), and a spray rate of 100 g/min to obtain a solid dispersion of the present invention.

Example 14

After 1000 g of compound A and 500 g of HPMC were dissolved in 13.5 kg of acetone and 1.5 kg of water (9:1), a spray dryer was used at an exhaust temperature of 60° C., a spray pressure of 0.3 MPa (BN160S-IS), and a spray rate of 50 g/min to obtain a solid dispersion of the present invention.

Example 15

After 1000 g of compound A and 500 g of HPMC were dissolved in 12.0 kg of acetone and 3.0 kg of water (8:2), a spray dryer was used at an exhaust temperature of 70° C., a spray pressure of 0.3 MPa (BN160S-IS), and a spray rate of 100 g/min to obtain a solid dispersion of the present invention.

Example 16

After 1000 g of compound A and 500 g of HPMC were dissolved in 12.0 kg of acetone and 3.0 kg of water (8:2), a spray dryer was used at an exhaust temperature of 60° C., a spray pressure of 0.3 MPa (BN160S-IS), and a spray rate of 50 g/min to obtain a solid dispersion of the present invention.

Example 17

After 2000 g of compound A and 1000 g of HPMC were dissolved in 27.0 kg of acetone and 3.0 kg of water (9:1), a spray dryer was used at an exhaust temperature of 65° C., a spray pressure of 0.4 MPa, and a spray rate of 50 g/min to obtain a solid dispersion of the present invention.

Example 18

After 2000 g of compound A and 1000 g of HPMC were dissolved in 27.0 kg of acetone and 3.0 kg of water (9:1), a spray dryer was used at an exhaust temperature of 65° C., a spray pressure of 0.4 MPa, and a spray rate of 75 g/min to obtain a solid dispersion of the present invention.

Example 19

After 2000 g of compound A and 1000 g of HPMC were dissolved in 27.0 kg of acetone and 3.0 kg of water (9:1), a spray dryer was used at an exhaust temperature of 65° C., a spray pressure of 0.4 MPa, and a spray rate of 100 g/min to obtain a solid dispersion of the present invention.

Example 20

After 2000 g of compound A and 1000 g of HPMC were dissolved in 27.0 kg of acetone and 3.0 kg of water (9:1), a spray dryer was used at an exhaust temperature of 60° C., a spray pressure of 0.4 MPa, and a spray rate of 75 g/min to obtain a solid dispersion of the present invention.

Example 21

After 2000 g of compound A and 1000 g of HPMC were dissolved in 27.0 kg of acetone and 3.0 kg of water (9:1), a spray dryer was used at an exhaust temperature of 70° C., a spray pressure of 0.4 MPa, and a spray rate of 75 g/min to obtain a solid dispersion of the present invention.

Example 22

After 667 g of compound A and 333 g of HPMC were dissolved in 6.0 kg of methylene chloride and 4.0 kg of methanol, a spray dryer was used at an exhaust temperature of 50° C., a spray pressure of 0.4 MPa, and a spray rate of 100 g/min to obtain a solid dispersion of the present invention.

Example 23

After 1334 g of compound A and 666 g of HPMC were dissolved in 18.0 kg of acetone and 2.0 kg of water (9:1), a spray dryer was used at an exhaust temperature of 60° C., a spray pressure of 0.4 MPa, and a spray rate of 100 g/min to obtain a solid dispersion of the present invention.

Example 24

After 1334 g of compound A and 666 g of HPMC were dissolved in 18.0 kg of acetone and 2.0 kg of water (9:1), a spray dryer was used at an exhaust temperature of 60° C., an rotary disk rotation speed of 20000 rpm, and a spray rate of 50 g/min to obtain a solid dispersion of the present invention.

Example 25

After 1334 g of compound A and 666 g of HPMC were dissolved in 18.0 kg of acetone and 2.0 kg of water (9:1), a spray dryer was used at an exhaust temperature of 75° C., an rotary disk rotation speed of 10000 rpm, and a spray rate of 75 g/min to obtain a solid dispersion of the present invention.

Example 26

After 500 g of compound A and 250 g of HPMC were dissolved in 6.75 kg of acetone and 1.25 kg of water (8.5:1.5), a spray dryer was used at an exhaust temperature of 70° C., a spray pressure of 0.3 MPa, and a spray rate of 100 g/min to obtain a solid dispersion of the present invention.

Example 27

After 3000 g of compound A and 1500 g of HPMC were dissolved in 40.5 kg of acetone and 4.5 kg of water (9:1), a spray dryer was used at an exhaust temperature of 70° C., a spray pressure of 0.3 MPa, and a spray rate of 100 g/min to obtain a solid dispersion of the present invention.

Example 28

After 3000 g of compound A and 1500 g of HPMC were dissolved in 40.5 kg of acetone and 4.5 kg of water (9:1), a spray dryer was used at an exhaust temperature of 70° C., a spray pressure of 0.3 MPa, and a spray rate of 100 g/min to obtain a solid dispersion of the present invention.

Example 29

After 1334 g of compound A and 666 g of HPMC were dissolved in 18.0 kg of acetone and 2.0 kg of water (9:1), a spray dryer was used at an exhaust temperature of 65° C., an rotary disk rotation speed of 10020 rpm, and a spray rate of 100 g/min to obtain a solid dispersion of the present invention.

Example 30

After 1334 g of compound A and 666 g of HPMC were dissolved in 18.0 kg of acetone and 2.0 kg of water (9:1), a spray dryer was used at an exhaust temperature of 60° C., an rotary disk rotation speed of 1020 rpm, and a spray rate of 100 g/min to obtain a solid dispersion of the present invention.

Example 31

After 1334 g of compound A and 666 g of HPMC were dissolved in 18.0 kg of acetone and 2.0 kg of water (9:1), a spray dryer was used at an exhaust temperature of 60° C., an rotary disk rotation speed of 15000 rpm, and a spray rate of 100 g/min to obtain a solid dispersion of the present invention.

Example 32

After 1334 g of compound A and 666 g of HPMC were dissolved in 18.0 kg of acetone and 2.0 kg of water (9:1), a spray dryer was used at an exhaust temperature of 60° C., an rotary disk rotation speed of 15000 rpm, and a spray rate of 140 g/min to obtain a solid dispersion of the present invention.

Example 33

After 3333 g of compound A and 1667 g of HPMC were dissolved in 45.0 kg of acetone and 5.0 kg of water (9:1), a spray dryer was used at an exhaust temperature of 60° C., an rotary disk rotation speed of 15000 rpm, and a spray rate of 100 g/min to obtain a solid dispersion of the present invention.

Example 34

After 125 g of compound A and 375 g of HPMC were dissolved in 4.5 kg of acetone and 0.5 kg of water (9:1), a spray dryer was used at an exhaust temperature of 68° C., a spray pressure of 0.3 MPa, and a spray rate of 100 g/min to obtain a solid dispersion of the present invention.

Example 35

After 667 g of compound A and 333 g of HPMC were dissolved in 9.0 kg of acetone and 1.0 kg of water (9:1), a spray dryer was used at an exhaust temperature of 65° C., a spray pressure of 0.3 MPa, and a spray rate of 100 g/min to obtain a solid dispersion of the present invention.

Example 36

After 667 g of compound A and 333 g of HPMC were dissolved in 9.0 kg of acetone and 1.0 kg of water (9:1), a spray dryer was used at an exhaust temperature of 67° C., a spray pressure of 0.1 MPa, and a spray rate of 100 g/min to obtain a solid dispersion of the present invention.

Example 37

After 667 g of compound A and 333 g of HPMC were dissolved in 9.0 kg of acetone and 1.0 kg of water (9:1), a spray dryer was used at an exhaust temperature of 66° C., an rotary disk rotation speed of 19970 rpm, and a spray rate of 100 g/min to obtain a solid dispersion of the present invention.

Example 38

After 667 g of compound A and 333 g of HPMC were dissolved in 9.0 kg of acetone and 1.0 kg of water (9:1), a spray dryer was used at an exhaust temperature of 68° C., an rotary disk rotation speed of 14980 rpm, and a spray rate of 100 g/min to obtain a solid dispersion of the present invention.

Example 39

After the solid dispersion prepared in Example 1 was mixed with a filler and magnesium stearate, a roller compactor (WP120×40V, manufactured by Alexanderwerk: the same roller compactor was used in the following examples) was used to obtain granules. After the resulting granules were mixed with a filler, a disintegrator, and magnesium stearate, the mixture was formed into tablets using a rotary tabletting machine, and the resulting tablets were coated by film coating to obtain a pharmaceutical composition of the present invention containing the solid dispersion.

Example 40

After the solid dispersion prepared in Example 3 was mixed with a filler and magnesium stearate, a roller compactor was used to obtain granules. After the resulting granules were mixed with a filler, a disintegrator, and magnesium stearate, the mixture was formed into tablets using a rotary tabletting machine, and the resulting tablets were coated by film coating to obtain a pharmaceutical composition of the present invention containing the solid dispersion.

Example 41

After the solid dispersion prepared in Example 4 was mixed with a filler and magnesium stearate, a roller compactor was used to obtain granules. After the resulting granules were mixed with a filler, a disintegrator, and magnesium stearate, the mixture was formed into tablets using a rotary tabletting machine to obtain a pharmaceutical composition of the present invention containing the solid dispersion.

Example 42

After 20 g of compound A and 10 g of HPMC were dissolved in 300 g of acetone, a spray dryer was used at an exhaust temperature of 70° C. and a spray rate of 6 g/min to obtain a solid dispersion of the present invention.

Example 43

After 20 g of compound A and 10 g of HPMC were dissolved in 285 g of acetone and 15 g of water, a spray dryer was used at an exhaust temperature of 70° C. and a spray rate of 6 g/min to obtain a solid dispersion of the present invention.

Example 44

After 20 g of compound A and 10 g of HPMC were dissolved in 270 g of acetone and 30 g of water, a spray dryer was used at an exhaust temperature of 70° C. and a spray rate of 6 g/min to obtain a solid dispersion of the present invention.

Example 45

After 20 g of compound A and 10 g of HPMC were dissolved in 240 g of acetone and 60 g of water, a spray dryer was used at an exhaust temperature of 70° C. and a spray rate of 6 g/min to obtain a solid dispersion of the present invention.

Example 46

After 20 g of compound A and 10 g of HPMC were dissolved in 210 g of acetone and 90 g of water, a spray dryer was used at an exhaust temperature of 70° C. and a spray rate of 6 g/min to obtain a solid dispersion of the present invention.

Example 47

After 10 g of compound A and 5 g of HPMC were dissolved in 180 g of acetone and 120 g of water, a spray dryer was used at an exhaust temperature of 70° C. and a spray rate of 6 g/min to obtain a solid dispersion of the present invention.

Example 48

After 2 g of compound A and 1 g of HPMC were dissolved in 150 g of acetone and 150 g of water, a spray dryer was used at an exhaust temperature of 70° C. and a spray rate of 6 g/min to obtain a solid dispersion of the present invention.

Example 49

After 20 g of compound A and 110 g of HPMC were dissolved in 270 g of acetone and 30 g of water, a spray dryer was used at an exhaust temperature of 50° C. and a spray rate of 6 g/min to obtain a solid dispersion of the present invention.

Example 50

After 20 g of compound A and 110 g of HPMC were dissolved in 270 g of acetone and 30 g of water, a spray dryer was used at an exhaust temperature of 60° C. and a spray rate of 6 g/min to obtain a solid dispersion of the present invention.

Example 51

After 20 g of compound A and 110 g of HPMC were dissolved in 270 g of acetone and 30 g of water, a spray dryer was used at an exhaust temperature of 80° C. and a spray rate of 6 g/min to obtain a solid dispersion of the present invention.

Example 52

After 20 g of compound A and 110 g of HPMC were dissolved in 270 g of acetone and 30 g of water, a spray dryer was used at an exhaust temperature of 90° C. and a spray rate of 6 g/min to obtain a solid dispersion of the present invention.

Example 53

After 20 g of compound A and 10 g of copolyvidone (Kollidon VA64, manufactured by BASF) were dissolved in 270 g of acetone and 30 g of water, a spray dryer was used at an exhaust temperature of 70° C. and a spray rate of 6 g/min to obtain a solid dispersion of the present invention.

Example 54

After 20 g of compound A and 10 g of HPC (HPC-L, manufactured by Shin-Etsu Chemical Co., Ltd.) were dissolved in 270 g of acetone and 30 g of water, a spray dryer was used at an exhaust temperature of 70° C. and a spray rate of 6 g/min to obtain a solid dispersion of the present invention.

Example 55

After 20 kg of compound A and 60 kg of HPMC were dissolved in 720 kg of acetone and 80 kg of water, a spray dryer was used at an exhaust temperature of 70° C. and a spray rate of 70 kg/hr to obtain a solid dispersion of the present invention.

Example 56

After the solid dispersion prepared in Example 44 was mixed with a filler and magnesium stearate, the mixture was formed into granules using a roller compactor. After the resulting granules were mixed with a filler, a disintegrator, and magnesium stearate, the mixture was formed into tablets using the single tabletting machine to obtain a pharmaceutical composition of the present invention containing the solid dispersion.

Example 57

After the solid dispersion prepared in Example 49 was mixed with a filler and magnesium stearate, the mixture was formed into granules using a roller compactor. After the resulting granules were mixed with a filler, a disintegrator, and magnesium stearate, the mixture was formed into tablets using the single tabletting machine to obtain a pharmaceutical composition of the present invention containing the solid dispersion.

Example 58

After the solid dispersion prepared in Example 50 was mixed with a filler and magnesium stearate, the mixture was formed into granules using a roller compactor. After the resulting granules were mixed with a filler, a disintegrator, and magnesium stearate, the mixture was formed into tablets using the single tabletting machine to obtain a pharmaceutical composition of the present invention containing the solid dispersion.

Example 59

After the solid dispersion prepared in Example 51 was mixed with a filler and magnesium stearate, the mixture was formed into granules using a roller compactor. After the resulting granules were mixed with a filler, a disintegrator, and magnesium stearate, the mixture was formed into tablets using the single tabletting machine to obtain a pharmaceutical composition of the present invention containing the solid dispersion.

Example 60

After the solid dispersion prepared in Example 52 was mixed with a filler and magnesium stearate, the mixture was formed into granules using a roller compactor. After the resulting granules were mixed with a filler, a disintegrator, and magnesium stearate, the mixture was formed into tablets using the single tabletting machine to obtain a pharmaceutical composition of the present invention containing the solid dispersion.

Comparative Example 1

After 1 part of compound A was mixed with 1 part of HPMC, a twin screw extruder was used at a screw rotation speed of 20 rpm and a treatment temperature of 190° C. to obtain a solid dispersion.

Comparative Example 2

After 1 part of compound A was mixed with 1 part of copolyvidone, a twin screw extruder was used at a screw rotation speed of 20 rpm and a treatment temperature of 185° C. to obtain a solid dispersion.

Experimental Example 1

Storage Stability Test

The solid dispersions prepared in Examples 1, 2, and 3, and Comparative Examples 1 and 2 were evaluated for stability. In this heat stability test, after the samples were put into bottles made of high-density polyethylene, respectively, the bottles were sealed and allowed to stand at 70° C. for 9 days. The amounts of analogous substances after 0, 5, and 9 days from the beginning of the storage are shown in Table 1. The stability was improved by controlling the ratio of water contained in each solvent. In this regard, the abbreviation "m.c." in Table 1 means a main component, i.e., the amount of a main degradation product of compound A.

TABLE 1

| Days for storage | Day 0 (% by weight) | Day 5 (% by weight) | Day 9 (% by weight) |
|---|---|---|---|
| Example 1 | Total: 0.11 m.c.: 0.09 | Total: 0.13 m.c.: 0.10 | Total: 0.15 m.c.: 0.12 |
| Example 2 | Total: 0.14 m.c.: 0.11 | Total: 0.22 m.c.: 0.20 | Total: 0.23 m.c.: 0.20 |

TABLE 1-continued

| Days for storage | Day 0 (% by weight) | Day 5 (% by weight) | Day 9 (% by weight) |
|---|---|---|---|
| Example 3 | Total: 0.28<br>m.c.: 0.28 | Total: 0.65<br>m.c.: 0.62 | Total: 0.79<br>m.c.: 0.76 |
| Comparative Example 1 | m.c.: 34.91% | — | — |
| Comparative Example 2 | m.c.: 9.78% | — | — |

With respect to the solid dispersions prepared in Examples 42, 43, 44, 45, 46, 47, and 48, and Comparative Examples 1 and 2, after the samples were put into bottles made of high-density polyethylene, respectively, the bottles were sealed and allowed to stand at 70° C. for 9 days. The amounts (% by weight) of analogous substances at the beginning of the storage and the amounts (% by weight) of a main degradation product after 9 days from the beginning of the storage are shown in Table 2.

TABLE 2

| Conditions for storage | Day 0 (% by weight) | 70° C., 9 days (% by weight) |
|---|---|---|
| Example 42 | 0.13 | 0.17 |
| Example 43 | 0.10 | 0.12 |
| Example 44 | 0.12 | 0.16 |
| Example 45 | 0.35 | 0.54 |
| Example 46 | 0.41 | 0.61 |
| Example 47 | 0.33 | 0.60 |
| Example 48 | 0.29 | 0.72 |
| Comparative Example 1 | 34.91 | — |
| Comparative Example 2 | 9.78 | — |

Experimental Example 2

Storage Stability Test

The pharmaceutical compositions prepared in Examples 39 and 40 were evaluated for stability. In this heat stability test, after the samples were packed into blister packs made from aluminum, respectively, the blister packs were allowed to stand at 25° C. and 60% relative humidity or at 40° C. and 75% relative humidity, for 30 days. The stability was improved by controlling the ratio of water contained in each solvent.

TABLE 3

| Conditions for storage | Day 0 (% by weight) | 25° C., 60% RH 30 days (% by weight) | 40° C., 75% RH 30 days (% by weight) |
|---|---|---|---|
| Example 39 | Total: 0.05<br>m.c.: 0.05 | Total: 0.06<br>m.c.: 0.06 | Total: 0.08<br>m.c.: 0.07 |
| Example 40 | Total: 0.35<br>m.c.: 0.33 | Total: 0.44<br>m.c.: 0.41 | Total: 0.81<br>m.c.: 0.79 |

Experimental Example 3

Specific Volume and Hardness of Solid Dispersions

The solid dispersions prepared in Examples 1, 5, 8, 13, 14, 17, 19, 23, 28, 44, 49, 50, 51, and 52 were evaluated for specific volume and hardness. The specific volume of each solid dispersion, and the hardness thereof are shown in Table 4 and FIG. 1. Solid dispersions having a large specific volume exhibited a high hardness.

TABLE 4

| | Specific volume (mL/g) | hardness (N) |
|---|---|---|
| Example 1 | 10.3 | 75 |
| Example 5 | 7.0 | 45 |
| Example 8 | 2.76 | 9 |
| Example 13 | 5.5 | 32 |
| Example 14 | 3.4 | 14 |
| Example 17 | 4.4 | 20 |
| Example 19 | 6.4 | 41 |
| Example 23 | 3.9 | 21 |
| Example 28 | 14.4 | 80 |
| Example 44 | 10.8 | 41 |
| Example 49 | 3.3 | 6 |
| Example 50 | 5.3 | 8 |
| Example 51 | 14.0 | 43 |
| Example 52 | 19.3 | 49 |

Experimental Example 4

Hardness of Tablets

Uncoated tablets prepared in Examples 39, 41, 56, 58, 59, and 60 were evaluated for tablet hardness. Tablets prepared by using a solid dispersion having a large specific volume exhibited a high hardness.

TABLE 5

| | Hardness (N) |
|---|---|
| Example 39 | 138 |
| Example 41 | 54 |
| Example 56 | 125 |
| Example 58 | 53 |
| Example 59 | 169 |
| Example 60 | 187 |

Experimental Example 5

X-Ray Analysis

Figure 6:
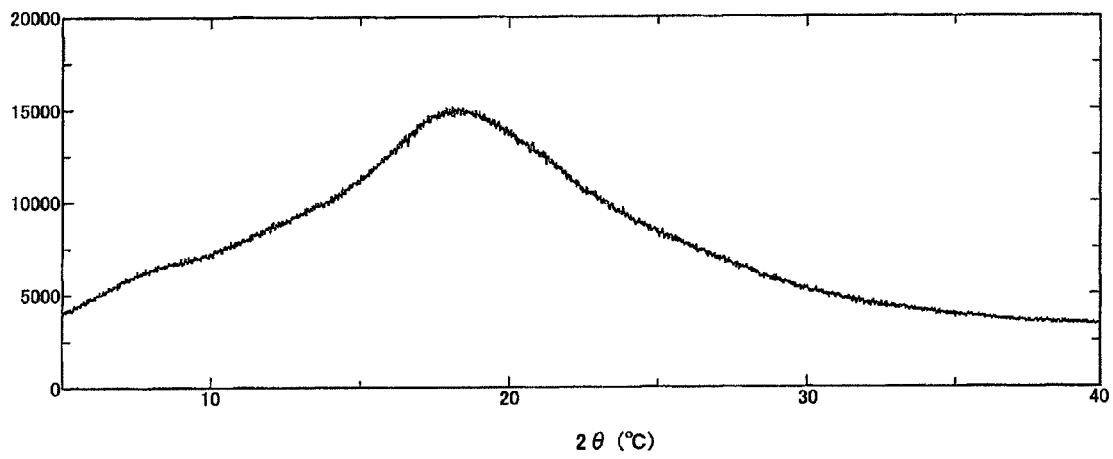
FIG. 6 is an X-ray diffraction spectrum of the solid dispersion which was prepared in Example 44 and stored at 70° C. for 9 days in Experimental Example 1.

The solid dispersions prepared in Examples 1, 44, 53, and 54, and the solid dispersion obtained by storing the solid dispersion prepared in Example 44 at 70° C. for 9 days in Experimental Example 1, were evaluated for crystallinity using X rays. As shown in FIGS. 2 to 5, the solid dispersions prepared in Examples 1, 44, 53, and 54 were amorphous. As shown in FIG. 6, the solid dispersion obtained by storing the solid dispersion prepared in Example 44 at 70° C. for 9 days in Experimental Example 1 was also amorphous.

Experimental Example 6

Solubility

Compound A, the solid dispersions prepared in Examples 44, 53, and 54, and the solid dispersion obtained by storing the solid dispersion prepared in Example 44 at 70° C. for 9 days in Experimental Example 1, were evaluated for solubility in accordance with the dissolution test described in the 15th Edition of the Japanese Pharmacopoeia. All solid dispersions prepared in these Examples exhibited an improved solubility compared to the original drug. The solid dispersion obtained by storing the solid dispersion prepared in Example 44 at 70° C. for 9 days in Experimental Example 1 exhibited the same solubility as that before the storage.

TABLE 6

|  | Solubility of compound A (µg/mL) |
|---|---|
| Compound A | 2 |
| Example 44 | 49 |
| Example 44 (70° C., 9 days) | 51 |
| Example 53 | 49 |
| Example 54 | 49 |

INDUSTRIAL APPLICABILITY

The present invention relates to a solid dispersion containing an amide derivative useful in preventing and treating diseases in which herpesviruses are involved and a water-soluble polymer, and a pharmaceutical composition containing the solid dispersion. The present invention can improve the solubility and oral absorption, and is useful for techniques capable of providing a stable and down-sizable pharmaceutical composition.

As above, the present invention was explained with reference to particular embodiments, but modifications and improvements obvious to those skilled in the art are included in the scope of the present invention.

The invention claimed is:

1. A pharmaceutical composition comprising a solid dispersion containing a compound of the general formula (I) or a salt thereof and a water-soluble polymer, wherein the pharmaceutical composition is not prepared by a melting method, and the water-soluble polymer is a polymer selected from the group consisting of hydroxypropylmethyl cellulose and copolyvidone, wherein the compound of general formula (I) has the formula:

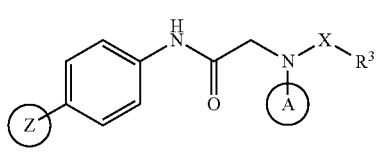

(I)

wherein Z is a member selected from the group consisting of a 1,2,4-oxadiazol-3-yl, and 4-oxazolyl;
A is a phenyl group which is substituted with at least one methyl group and may further have 1 to 2 substituents selected from the group consisting of a methyl group and a halogen atom;
X is CO;
$R^3$ is a 1,1-dioxide tetrahydro-2H-thiopyran-4-yl group; and wherein the amount of the water-soluble polymer is 0.1 to 10 parts by weight, with respect to 1 part by weight of the compound of the general formula (I).

2. The pharmaceutical composition according to claim 1, wherein
Z is a 1,2,4-oxadiazol-3-yl; and
A is a phenyl which is substituted with at least one methyl group and may further have 2 substituents selected from the group consisting of a methyl group and a halogen atom.

3. The pharmaceutical composition according to claim 1, wherein the compound of the formula (I) is a compound selected from the group consisting of:
N-(4-methylphenyl)-N-(2-{[4-(1,3-oxazol-4-yl)phenyl]amino}-2-oxoethyl)tetrahydro-2H-thiopyran-4-carboxamide 1,1-dioxide);
N-(4-methylphenyl)-N-(2-{[4-(1,2,4-oxadiazol-3-yl)phenyl]amino}-2-oxoethyl)tetrahydro-2H-thiopyran-4-carboxamide 1,1-dioxide;
N-(2,6-dimethylphenyl)-N-(2-{[4-(1,2,4-oxadiazol-3-yl)phenyl]amino}-2-oxoethyl)tetrahydro-2H-thiopyran-4-carboxamide 1,1-dioxide;
N-(3-fluoro-4-methylphenyl)-N-(2-{[4-(1,2,4-oxadiazol-3-yl)phenyl]amino}-2-oxoethyl)tetrahydro-2H-thiopyran-4-carboxamide 1,1-dioxide; and
N-(4-chloro-3-methylphenyl)-N-(2-{[4-(1,2,4-oxadiazol-3-yl)phenyl]amino}-2-oxoethyl)tetrahydro-2H-thiopyran-4-carboxamide 1,1-dioxide.

4. The pharmaceutical composition according to claim 1, wherein the compound of the formula (I) is
N-(2,6-Dimethylphenyl)-N-(2-{[4-(1,2,4-oxadiazol-3-yl)phenyl]amino}-2-oxoethyl)tetrahydro-2H-thiopyran-4-carboxamide 1,1-dioxide.

5. The pharmaceutical composition according to claim 1, wherein the amount of the water-soluble polymer is 0.1 to 5 parts by weight, with respect to 1 part by weight of the compound of the formula (I).

6. The pharmaceutical composition according to claim 1, wherein the specific volume of the solid dispersion is 2 to 25 mL/g.

7. The pharmaceutical composition according to claim 1, wherein a tablet hardness is 5 to 300 N when 100 mg of the solid dispersion is formed into tablets using a flat punch of 7.5 mm in diameter under a tabletting pressure of 2 kN.

8. The pharmaceutical composition according to claim 1, further comprising a disintegrator.

9. The pharmaceutical composition according to claim 1, prepared by a process comprising the steps of:
dissolving and/or suspending the compound of the formula (I) and the water-soluble polymer in a pharmaceutically acceptable solvent, and
removing the solvent by spray drying to prepare the solid dispersion.

10. The pharmaceutical composition according to claim 9, wherein the pharmaceutically acceptable solvent is one solvent, or two or more solvents selected from the group consisting of ketones, alcohols, and water.

11. The pharmaceutical composition prepared by the process described in claim 10, wherein the pharmaceutically acceptable solvent is a mixture of ketones, alcohols, or a mixed solvent thereof, with water, and the content of water in the pharmaceutically acceptable solvent is more than 0% by weight to less than 50% by weight.

* * * * *